(12) United States Patent
Kawase et al.

(10) Patent No.: US 7,981,265 B2
(45) Date of Patent: Jul. 19, 2011

(54) GAS CONCENTRATION MEASURING APPARATUS DESIGNED TO ENHANCE MEASUREMENT ACCURACY IN DESIRED RANGE

(75) Inventors: Tomoo Kawase, Aichi-ken (JP); Eiichi Kurokawa, Okazaki (JP); Satoshi Hada, Inazawa (JP); Toshiyuki Suzuki, Handa (JP); Katsuhide Akimoto, Nishio (JP)

(73) Assignee: Denso Corporation, Kariya (JP)

( * ) Notice: Subject to any disclaimer, the term of this patent is extended or adjusted under 35 U.S.C. 154(b) by 315 days.

(21) Appl. No.: 11/797,961

(22) Filed: May 9, 2007

(65) Prior Publication Data

US 2007/0284248 A1    Dec. 13, 2007

(30) Foreign Application Priority Data

May 26, 2006  (JP) ................. 2006-146392

(51) Int. Cl.
    *G01N 27/41*    (2006.01)
(52) U.S. Cl. ...................... 204/425; 204/406
(58) Field of Classification Search .......... 204/400–435; 205/775–794.5
    See application file for complete search history.

(56) References Cited

U.S. PATENT DOCUMENTS

| | | | |
|---|---|---|---|
| 4,914,424 A | | 4/1990 | Hirao et al. |
| 5,721,513 A | * | 2/1998 | Yuasa ............................ 330/282 |
| 5,980,710 A | * | 11/1999 | Kurokawa et al. ............ 204/425 |
| 5,980,728 A | | 11/1999 | Farber et al. |
| 6,226,861 B1 | | 5/2001 | Kurokawa et al. |
| 6,497,135 B1 | | 12/2002 | Sanders et al. |
| 2004/0089545 A1 | | 5/2004 | Kawase et al. |

FOREIGN PATENT DOCUMENTS

| | | |
|---|---|---|
| EP | 1 452 861 A2 | 9/2004 |
| JP | 2004-205488 | 7/2004 |

OTHER PUBLICATIONS

EPO Extended Search Report mailed Sep. 20, 2007 in Application No. 07106934.8.

\* cited by examiner

*Primary Examiner* — Kaj K Olsen
*Assistant Examiner* — Susan Thai
(74) *Attorney, Agent, or Firm* — Nixon & Vanderhye P.C.

(57) ABSTRACT

A gas concentration measuring apparatus for use in air-fuel ratio control of automotive engines is designed to determine the concentration of oxygen within a wide and a narrow range using a sensor current flowing through a sensor element. The apparatus includes an amplifier circuit equipped with an operational amplifier and a plurality of amplifying resistors and a switch. The switch is responsive to a request signal to switch a relation in electrical connection between an operational amplifier and the amplifying resistors to distribute the amplifying resistors into an input resistor and a feedback resistor for the operational amplifier to change an amplification factor of the amplifier circuit. This results in a change in resolution of measurement of the concentration of oxygen, thereby ensuring enhanced accuracy in determining the concentration of oxygen in a selected one of the narrow and wide ranges.

6 Claims, 8 Drawing Sheets

GAS CONCENTRATION MEASURING APPARATUS DESIGNED TO ENHANCE MEASUREMENT ACCURACY IN DESIRED RANGE

CROSS REFERENCE TO RELATED DOCUMENT

The present application claims the benefit of Japanese Patent Application No. 2006-146392 filed on May 26, 2006 the disclosures of which are incorporated herein by reference.

BACKGROUND OF THE INVENTION

1. Technical Field of the Invention

The invention relates generally to a gas concentration measuring apparatus which may be used in measuring the concentration of a preselected component, such as oxygen, of exhaust emissions of automotive engines, and more particularly to such a gas concentration measuring apparatus designed to ensure enhanced accuracy in determining the concentration of gas in a desired measuring range.

2. Background Art

There are known gas concentration measuring apparatuses designed as air-fuel ratio measuring apparatuses to measure the concentration of oxygen ($O_2$) contained in exhaust gas emitted from an automotive engine to determine an air-fuel ratio of a mixture charged into the engine for use in air-fuel ratio control systems implemented by, for example, an engine ECU (Electronic Control Unit). The engine ECU works to perform stoichiometric air fuel ratio control to bring the air-fuel ratio to around the stoichiometry in the feedback mode or lean air-fuel ratio control to bring the air-fuel ratio to within a lean range. In recent years, emission regulations or on-board diagnostic (OBD) requirements have been increasingly tightened. Improvement of the stoichiometric air-fuel ratio control is, thus, being sought. Additionally, there is an increasing need for expanding an air-fuel ratio measuring range up to an atmospheric range as well as the lean range that is a typical air-fuel ratio controlling range. For instance, a sensor malfunction monitoring system is required to meet the OBD requirements which works to monitor a deterioration of a gas sensor such as clogging resulting in a decrease in sensor output current during a fuel cut-off (i.e., when exhaust gasses are equivalent to air) under a given operating engine condition. It is also essential to improve fuel efficiency as well as exhaust emissions. It is further essential to feedback-control a rich mixture at high load engine operating conditions.

In order to enhance the accuracy in measuring the air-fuel ratio, Japanese Patent First Publication No. 2004-205488 teaches installation of a plurality of amplifiers different in amplification factor from each other in an output stage of a sensor control circuit for improving the accuracy in determining the air-fuel ratio within two ranges: a wide air-fuel measuring range and a narrow air-fuel ratio measuring range, as defined in a limited area of the wide air-fuel ratio measuring range.

The above system, however, has the disadvantage that the use of the plurality of amplifiers (operational amplifiers) results in increases in size of the sensor control circuit and number of input/output terminals used in the sensor control circuit. This approach has still left room for improvement.

SUMMARY OF THE INVENTION

It is therefore a principal object of the invention to avoid the disadvantages of the prior art.

It is another object of the invention to provide a simplified structure of a gas concentration measuring apparatus designed to have enhanced accuracy in determining the concentration of gas in a desired measuring range.

According to one aspect of the invention, there is provided a gas concentration measuring apparatus which may be employed in determining an air-fuel ratio of a mixture supplied to an automotive engine for use in combustion control of the engine. The gas concentration measuring apparatus comprises: (a) a gas sensor equipped with a sensor element which is made of a solid electrolyte and works to produce a sensor current upon application of voltage thereto as a function of a concentration of a selected gas; (b) a current-measuring resistor used to measure the sensor current flowing through the sensor element; (c) an amplifier circuit equipped with an operational amplifier and a plurality of amplifying resistors, the amplifier circuit working to amplify the sensor current, as measured through the current-measuring resistor; (d) a gas concentration measuring circuit working to determine the concentration of the gas based on the sensor current, as amplified by the amplifier circuit; and (e) a switch designed to switch a relation in electrical connection between the operational amplifier and the amplifying resistors to distribute the amplifying resistors into an input resistor and a feedback resistor for the operational amplifier to change an amplification factor of the amplifier circuit. This results in a change in resolution of measurement of the concentration of the gas. Required accuracy in measuring the concentration of the gas in a desired measuring range is, therefore, achieved by controlling the switching operation of the switch to change the amplification factor of the amplifier circuit without need for complexity of the structure.

In the preferred mode of the invention, the switch is disposed on an input line extending from the current-measuring resistor and the operational amplifier. Specifically, the input line to the operational amplifier has typically a high impedance, so that a resistance component of the switch may be ignored, thus resulting in improved accuracy in amplifying the sensor current.

The gas concentration measuring circuit may be designed to determine the concentration of the gas in a selected one of a plurality of measuring ranges. When it is required to select a narrower one of the measuring ranges, the gas concentration measuring circuit controls an operation of the switch so as to increase the amplification factor of the amplifier circuit. When it is required to selected a wider one of the measuring ranges, the gas concentration measuring circuit controls the operation of the switch so as to decrease the amplification factor of the amplifier circuit.

The amplifying resistors may be implemented by three resistors connected in series. The switch works to select at least one of the resistors as the input resistor and the other resistors as the feedback resistor.

The gas concentration measuring apparatus may further include an input line extending from the current-measuring resistor and the operational amplifier. The input line includes a first and a second branch line which extend parallel to each other. The first branch line has at least one of the amplifying resistors and the switch disposed thereon. The second branch line has the other amplifying resistors disposed thereon. Specifically, the second branch line servers as an always-on connection line which connects the operational amplifier and any of the amplifying resistors constantly without the switch, thus avoiding temporal opening of the input line to the amplifier circuit upon switching of the switch. This ensures the stability of the sensor current to be outputted by the amplifier circuit.

The selected gas may be a selected gas component in exhaust emissions from an internal combustion engine. The gas concentration measuring apparatus calculates the concentration of the selected gas component for determining an air-fuel ratio of a mixture charged into the internal combustion engine in a selected one of a narrow range defined around a stoichiometric air-fuel ratio and a wide range which is wider than the narrow range and extends from a fuel rich air-fuel ratio to a fuel lean air-fuel ratio. The gas concentration measuring circuit controls the operation of the switch so as to have amplification factors in the amplifier circuit which are different between the narrow and wide ranges.

The wide range may be defined to include at least one of an atmospheric air-equivalent value when the internal combustion engine is undergoing a fuel cut and a value of an air-fuel ratio during rich air-fuel ratio burning of the internal combustion engine. This enables the gas sensor to be diagnosed using a measured value of the air-fuel ratio during the fuel cut of the engine and rich feedback control to be performed correctly when the load on the engine is increasing during acceleration of the engine.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 5($b$) is a time chart which demonstrates switching between wide and narrow air-fuel ratio measuring ranges;

FIG. 5($c$) is a time chart which demonstrates a switching operation for electing one of the wide and narrow air-fuel ration measuring ranges in FIG. 5($b$);

FIG. 5($d$) is a time chart which demonstrates switching between amplification factors, as achieved by the switching operation in FIG. 5($c$);

FIG. 7($b$) is a circuit diagram which shows a modified structure of the sensor control circuit in FIG. 7($a$);

FIG. 8($b$) is a transverse sectional view which shows a sensor element of a gas concentration measuring apparatus according to the fifth embodiment of the invention;

DESCRIPTION OF THE PREFERRED EMBODIMENTS

Figure 1:
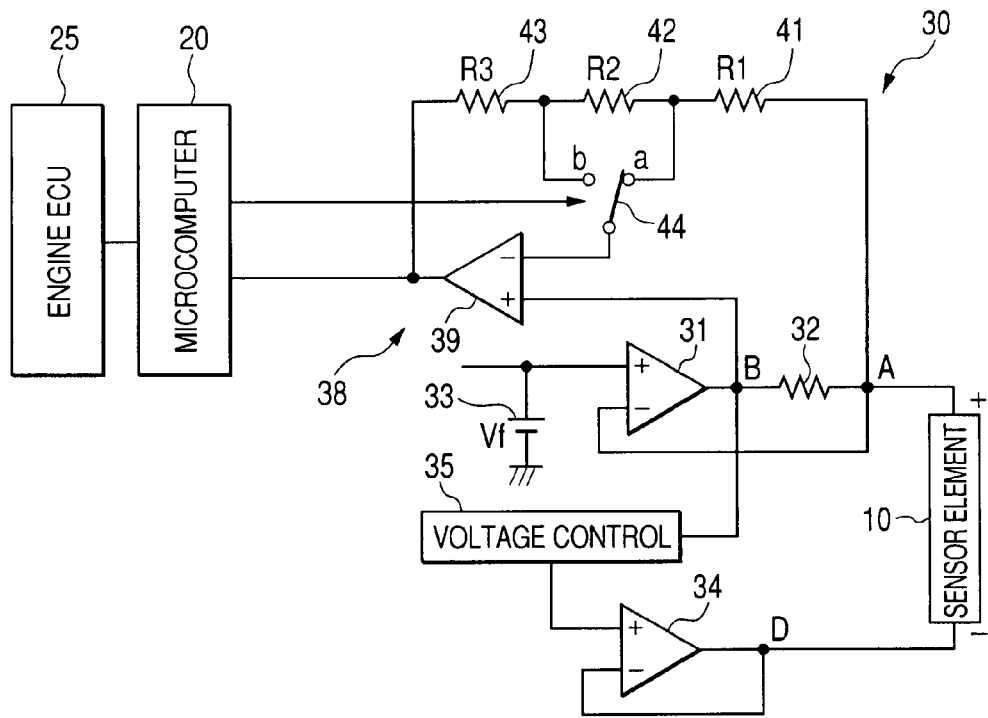
FIG. 1 is a circuit diagram which shows an electric structure of a gas concentration measuring apparatus according to the first embodiment of the invention.

Referring to the drawings, wherein like reference numbers refer to like parts in several views, particularly to FIG. 1, there is shown a gas concentration measuring apparatus designed as an air-fuel ratio measuring apparatus to measure the concentration of oxygen ($O_2$) contained in exhaust emissions of an automotive engine that is a function of an air-fuel ratio (AFR) of a mixture charged into the engine. The measured concentration is used in an air-fuel ratio control system implemented by an engine electronic control unit (ECU). The air-fuel ratio control system works to perform stoichiometric air-fuel ratio control to regulate the air-fuel ratio of the mixture around the stoichiometry in the feedback mode and lean air-fuel ratio control to bring the air-fuel ratio to within a given lean range in the feedback mode. The air-fuel ratio measuring apparatus of this embodiment is designed to measure the air-fuel ratio over a wide range extending from a rich range (e.g., A/F=11:1) to an atmospheric range in order to enable control of the air-fuel ratio meeting future emission regulations or on-board diagnostic (OBD) requirements, rich air-fuel ratio control in a rich burning mode of engine operation, or control of releasing NOx trapped in a NOx absorber catalyst installed in an exhaust system of the engine or reviving the NOx absorber catalyst poisoned by sulfur.

The air-fuel ratio measuring apparatus includes an oxygen sensor (will be referred to as an air-fuel (A/F) sensor below) which works to produce a current signal as a function of concentration of oxygen contained in exhaust emissions introduced into a gas chamber formed in the A/F sensor.

Figure 2:
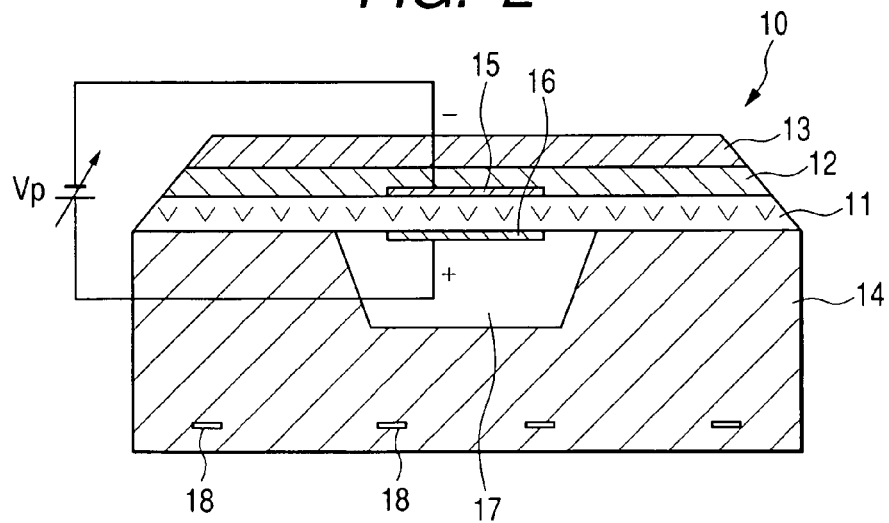
FIG. 2 is a transverse sectional view which shows a sensor element used in the gas concentration measuring apparatus as illustrated in FIG. 1.

The A/F sensor includes a laminated sensor element 10 which has a sectional structure, as illustrated in FIG. 2. The sensor element 10 has a length extending perpendicular to the drawing surface of FIG. 2 and is, in practice, disposed within a sensor housing and a protective cover. The A/F sensor is installed in an exhaust pipe of the engine. For instance, EPO 987 546 A2, assigned to the same assignee as that of this application teaches a structure and control of an operation of this type of gas sensor in detail, disclosure of which is incorporated herein by reference.

The sensor element 10 is made up of a solid electrolyte layer 11, a diffusion resistance layer 12, a shielding layer 13, and an insulating layer 14 which are laminated or stacked vertically as viewed in the drawing. The sensor element 10 is surrounded by a protective layer (not shown). The solid electrolyte layer 11 is made of a rectangular partially-stabilized zirconia sheet and has upper and lower electrodes 15 and 16 affixed to opposed surfaces thereof. The electrodes 15 and 16 are made of platinum (Pt), for example. The diffusion resistance layer 12 is made of a porous sheet which permits exhaust gasses to flow to the electrode 15. The shielding layer 13 is made of a dense sheet which inhibits the exhaust gasses from passing therethrough. The layers 12 and 13 are each formed using a sheet made of ceramic such as alumina, zirconia or spinel and have average porosities, or gas permeability different from each other.

The insulating layer 14 is made of highly thermal conductive ceramic such as alumina and has formed therein an air duct 17 to which the electrode 16 is exposed. The insulating layer 14 has a heater 18 embedded therein. The heater 18 is made of heating wire which is supplied with power from a storage battery installed in the vehicle to heat the whole of the sensor element 10 up to a desired activation temperature. In the following discussion, the electrode 15 will also be referred to as a diffusion resistance layer side electrode, and the electrode 16 will also be referred to as an atmosphere side electrode. The atmosphere side electrode 16 is connected to a positive (+) terminal of a power source Vp, while the diffusion resistance layer side electrode 15 is connected to a negative (−) terminal of the power source Vp.

The exhaust gas flowing within the exhaust pipe of the engine to which the sensor element 10 is exposed enters and passes through the side of the diffusion resistance layer 12 and reaches the diffusion resistance layer side electrode 15. When the exhaust gas is in a fuel lean state (more oxygen), oxygen molecules contained in the exhaust gas is decomposed or ionized by application of voltage between the electrodes 15 and 16, so that they are discharged to the air duct 17 through the solid electrolyte layer 11 and the electrode 16. Alternatively, when the exhaust gas is in a fuel rich state (less oxygen), oxygen molecules contained in air within the air duct 17 are ionized by the electrode 16 so that they are discharged into the exhaust pipe through the solid electrolyte layer 11 and the electrode 15. The operation of the A/F sensor is well known in the art, and explanation thereof in detail will be omitted here.

Figure 3:
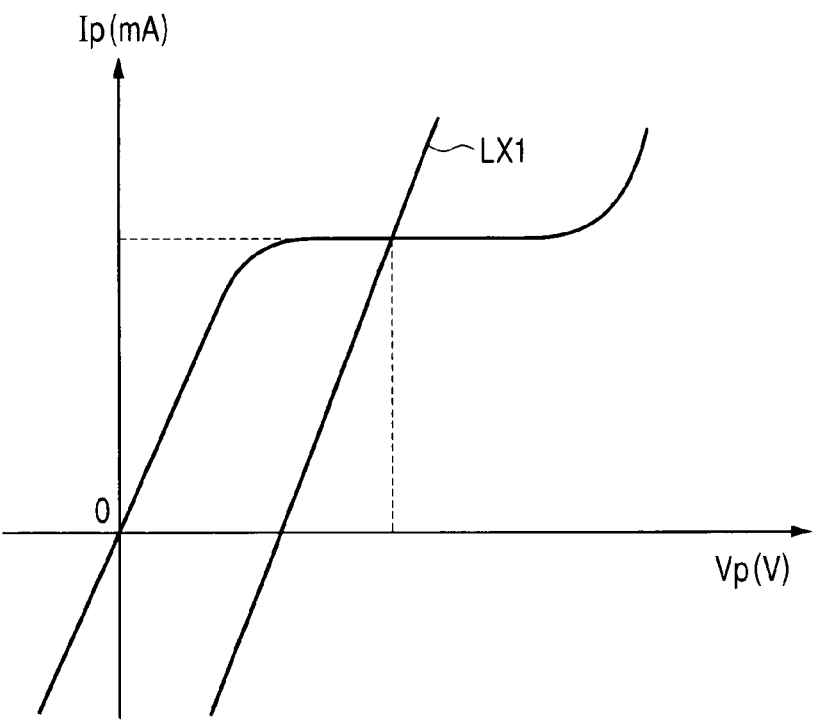
FIG. 3 shows an example of an applied voltage-to-output current map for use in determining a target voltage to be applied to the sensor element as illustrated in FIG. 2.

FIG. 3 shows a typical voltage-to-current relation (i.e., V-I characteristic) of the A/F sensor. A straight segment of a V-I curve extending parallel to the abscissa axis (i.e., V-axis) indicate a limiting current range within which the sensor element 10 produces an electric current Ip (i.e., a limiting current) as a function of an air-fuel ratio (i.e., richness or leanness). Specifically, as the air-fuel ratio changes to the lean side, the current Ip produced by the sensor element 10 increases, while as the air-fuel ratio changes to the rich side, the current Ip decreases. The current Ip will also be referred to as a sensor element current below. A line LX1 indicates a target voltage Vp to be applied to the sensor element 10 (i.e., the electrodes and 16). An inclination of the line LX1 is substantially identical with that of a portion of the V-I curve lower in voltage than the limiting current range.

Referring back to FIG. 1, the air-fuel ratio measuring apparatus includes a sensor control circuit 30 and a microcomputer and works to control an operation of the A/F sensor to measure the sensor element current Ip and to determine an air-fuel (A/F) ratio of a mixture charged to the engine using the sensor element current Ip. The microcomputer 20 is made of a known arithmetic logic unit consisting of a CPU, memories, and A/D converters and works to sample an A/F output voltage, as produced by the sensor control circuit 30 based on the sensor element current Ip, through the A/D converter to calculate the concentration of oxygen in the exhaust gas to determine the value of an A/F ratio of the mixture charged into the engine. The A/D converter is designed to have, for example, a resolution of 10 bits and operate on a voltage within a range of 0 to 5V. The A/F ratio, as determined by the microcomputer 20, is outputted in real time to an engine ECU 25 for use in the air-fuel ratio feedback control.

The engine ECU 20 is equipped with a stoichiometric feedback control function, as performed during normal running of the vehicle, a rich feedback control function, as performed when it is required to highly increase loads on the engine, and a sensor diagnosis function, as performed when the A/F sensor is placed in an atmospheric condition arising from cut of fuel to the engine. These functions all use an actual value of the A/F ratio, that is, an output of the A/F sensor.

More specifically, when it is required to perform the stoichiometric feedback control function, the ECU 25 works to determine a stoichiometric value (i.e., A/F=14.7:1) as a target air-fuel ratio and control the quantity of fuel to be sprayed by injectors to bring an actual value of the A/F ratio, as sampled by the A/F sensor, into agreement with the target air-fuel ratio (which is also referred to as fine stoichiometric control). When it is required to increase loads on the engine, that is, when it is required to accelerate the vehicle or the vehicle is climbing on a slope, the ECU 20 starts to perform the rich feedback control function and determines a fuel rich value (e.g., A/F=10:1) as the target air-fuel ratio to control the quantity of fuel to be sprayed by the injectors to bring an actual value of the A/F ratio, as sampled by the A/F sensor, into agreement with the target air-fuel ratio. When it is required to perform the sensor diagnosis function to diagnose the A/F sensor during the fuel-cut mode of engine operation, and the gas atmosphere within the exhaust pipe of the engine has become the air atmosphere (i.e., a known atmosphere) due to the fuel cut of the engine, the ECU 25 determines whether an output of the A/F sensor (i.e., the sensor element current Ip) has a value representing the air atmosphere or not. If not, the ECU 25 determines that the A/F sensor has deteriorated so that it is malfunctioning.

Figure 4:
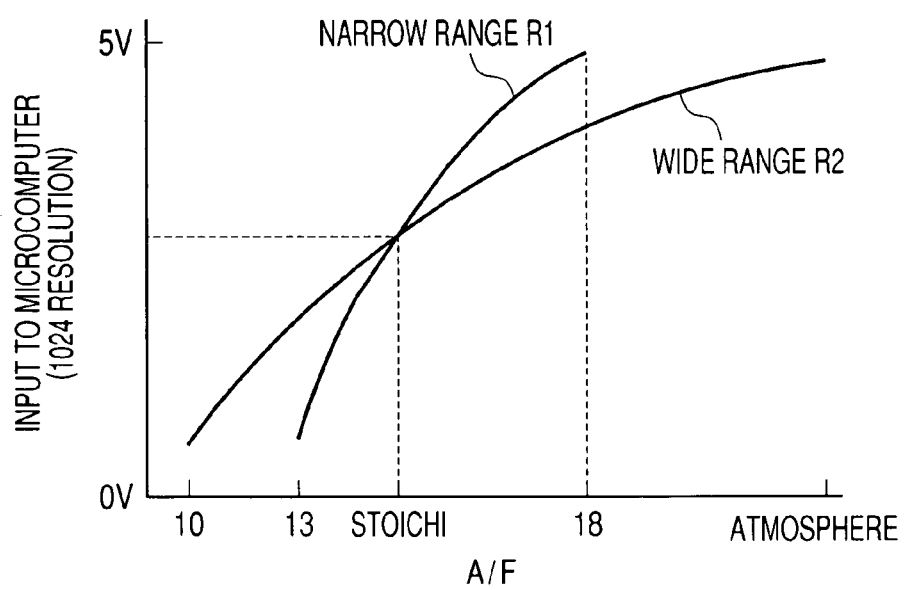
FIG. 4 is a view which shows relations between an air-fuel ratio and an input to a microcomputer in narrow and wide air-fuel ratio measuring ranges.
Figure 5:
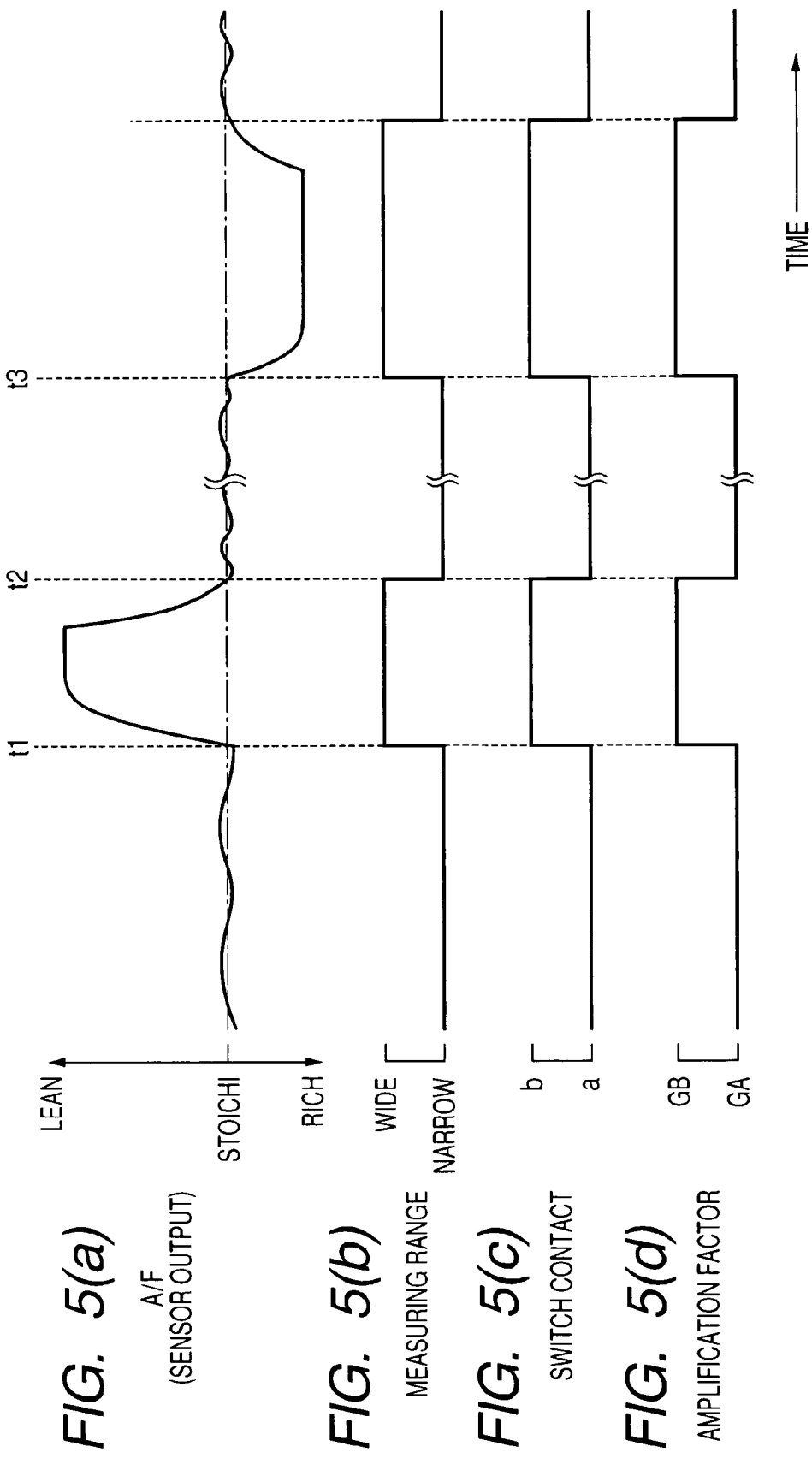
FIG. 5($a$) is a time chart which demonstrates a change in air-fuel ratio or an output of an A/F sensor.

The stoichiometric feedback control requires highly accurate measurement of the air-fuel ratio in a near-stoichiometric range including the stoichiometric air fuel ratio, while the rich feedback control or the sensor diagnosis requires measurement of the air-fuel ratio in a wide range extending from the rich range to the extreme lean range (i.e., an atmospheric range). In order to meet this requirement, the microcomputer 20 is designed to switch between two air-fuel ratio measuring ranges: a narrow range R1, as defined near the stoichiometric air fuel ratio, and a wide range R2, as defined to extend from the rich range to the extreme lean range, depending upon the type of a selected one of air-fuel ratio control tasks to be performed in the engine ECU 25. In the narrow range R1, the microcomputer 20 is permitted to determine the air-fuel ratio at enhanced resolutions within a limited voltage range (i.e., an operating voltage range of the A/D converters of the microcomputer 20). In the wide range R2, the microcomputer 20 is permitted to determine the air-fuel ratio over the whole of a range required by the engine ECU 25. FIG. 4 represents relations between the air-fuel ratio and an input to the microcomputer 20 in the narrow and wide ranges R1 and R2. The narrow range R1 is between A/F ratio=13:1 and A/F ratio=18:1. The wide range R2 is between A/F ratio=10:1 and the atmospheric air-equivalent value that is the value of the air-fuel ratio in the case the A/F sensor is placed in the exhaust gas equivalent in concentration of oxygen to the atmospheric air.

The stoichiometric feedback control, the rich feedback control, and the sensor diagnosis are not to be performed simultaneously, but selectively, thus not requiring simultaneous measurements of the air fuel ratio in the narrow range R1 and the wide range R2. The microcomputer 20 works to select one of the narrow range R1 and the wide range R2, as requested, to calculate the value of the air-fuel ratio in the selected one of the narrow and wide ranges R1 and R2.

The sensor control circuit 30 connects with the sensor element 10 through a positive (+) terminal and a negative (−) terminal. The positive terminal leads to the atmosphere side electrode 16 of the sensor element 10, while the negative terminal leads to the diffusion resistance layer side electrode 15. The sensor control circuit 30 also includes operational amplifiers 31 and 34, a current-measuring resistor 32, a reference voltage source 33, and a voltage application control circuit 35. The positive terminal of the sensor element 10 also connects with the reference voltage circuit 33 through the current-measuring resistor 32 and the operational amplifier 31. The negative terminal also connects with the voltage application control circuit 35 through the operational amplifier 34. The voltage appearing at a junction A of an end of the current-measuring resistor 32 and the positive terminal of the sensor element 10 is kept at the same level as that of the reference voltage source 33 (i.e., a reference voltage Vf). The sensor element current Ip flows through the current-measuring resistor 32. The voltage appearing at a junction B changes with a change in the sensor element current Ip. When the exhaust gas of the engine is in a fuel lean state, that is, the exhaust gas results from burning of a lean mixture, the sensor element current Ip flows from the positive terminal to the negative terminal through the sensor element 10, so that the voltage at the junction B rises. Conversely, when the exhaust gas is a fuel rich state, the sensor element current Ip flows from the negative terminal to the positive terminal through the sensor element 10, so that the voltage at the junction B drops. The voltage application control circuit 35 works to monitor the voltage at the junction B and determine the target voltage Vp to be applied to the sensor element 10 as a function of the monitored voltage, for example, by look-up using the target applying voltage line LX1, as illustrated in FIG. 3. The voltage application control circuit 35 then controls the operational amplifier 34 to bring the voltage at the junction D into agreement with the target voltage Vp. If it is required only to measure the A/F ratio (i.e., the sensor element current Ip) near the stoichiometric one, the voltage application control circuit 35 may keep the voltage to be applied to the sensor element 10 at a constant level.

The sensor control circuit 30 also has an amplifier circuit 38 connected between the junctions A and B across the current-measuring resistor 32. The amplifier circuit 38 works to produce an output (will also be referred to as an A/F output voltage below) which is in turn inputted to an input terminal of the A/D converter of the microcomputer 20. The microcomputer 20 analyzes the A/F output voltage, as converted into a digital form by the A/D converter, and determines the A/F ratio of the mixture charged into the engine. The amplifier circuit 38 is made up of an operational amplifier 39, series-connected amplifying resistors 41, 42, and 43, and a switch 44 made of, for example, a MOS transistor. The resistors 41, 42, and 43 have resistance values R1, R2, and R3, respectively.

The switch 44 is disposed on a signal input line connecting with a minus (−) input terminal (i.e., an inverting input terminal). The switch 44 has two contacts a and b connecting with ends of the resistor 42 that is a middle one of the resistors 41 to 43. In a normal mode of operation, the switch 44 establishes, as illustrated in the drawing, an electrical connection between the minus input terminal of the operational amplifier 39 and the contact a. When a range switching request signal is inputted from the microcomputer 20, the switch 44 establishes an electrical connection between the minus input terminal of the operational amplifier 39 and the contact b.

When the minus input terminal of the operational amplifier 39 is connected to the contact a, the amplifying resistor 41 serves as an input resistor in the amplifier circuit 38, and the amplifying resistors 42 and 43 serve as a feedback resistor in the amplifier circuit 38. The amplification factor GA of the amplifier circuit 38 in such a condition will, thus, be given by an equation below.

$$GA=(R2+R3)/R1 \qquad (1)$$

Alternatively, when the minus input terminal of the operational amplifier 39 is connected to the contact b, the amplifying resistors 41 and 42 serve as the input resistor in the amplifier circuit 38, and the amplifying resistor 43 serves as the feedback resistor in the amplifier circuit 38. The amplification factor GB of the amplifier circuit 38 in such a condition will, thus, be given by an equation below.

$$GB=R3/(R1+R2) \qquad (2)$$

Comparison between the equations (1) and (2) shows that the amplification factor GA is greater than the amplification factor GB. Specifically, when the connection of the minus input terminal of the operational amplifier 38 to the contact a is switched to the contact b, it will cause the amplification factor of the amplifier circuit 38 to be changed from a higher one to a lower one. In this embodiment, when the switch 44 establishes the electrical connection between the operational amplifier 39 and the contact a, the amplification factor GA is set to ×15, while when the switch 44 establishes the electrical connection between the operational amplifier 39 and the contact b, the amplification factor GB is set to ×5.

In operation, the microcomputer 20 receives an air-fuel ratio measuring range selection request, as provided depending upon the type of a control task to be performed by the engine ECU 25, and outputs the range switching request signal to the switch 44 to establish the electrical connection of the operational amplifier 39 to the contact a or b. When it is required to measure the air-fuel ratio in the narrow range R1, the microcomputer 20 works to connect the amplifier 39 to the contact a to increase the amplification factor of the amplifier circuit 38 to enhance the resolution of the measurement of the air-fuel ratio. Alternatively, when it is required to measure the air-fuel ratio in the wide range R2, the microcomputer 20 works to connect the amplifier 39 to the contact b to decrease the amplification factor of the amplifier circuit 38 to widen the air-fuel ratio measuring range thereof.

FIGS. 5(a) to 5(d) demonstrate selection of the air-fuel ratio measuring range (i.e., the narrow range R1 or the wide range R2) of the microcomputer 20, the contact a or b of the switch 44, and the amplification factor GB or GA in response to a change in air-fuel (A/F) ratio.

Before time t1, the engine ECU 25 is performing the stoichiometric feedback control. The A/F ratio (i.e., an output of the A/F sensor) is kept near stoichiometric. The microcomputer 20 sets the air-fuel ratio measuring range thereof to the narrow range R1. The sensor control circuit 30 controls the switch 44 and establishes the electrical connection between the operational amplifier 39 and the contact a to select a higher one (i.e., GA) of the amplification factors GB and GA. This enables fine measurement of the A/F ratio around the stoichiometric air-fuel ratio, thereby achieving the stoichiometric feedback control finely.

When the vehicle has been decelerated, and the fuel to be supplied to the engine is cut at time t1, it will cause the gas atmosphere in the exhaust pipe of the engine to be the air atmosphere, so that the A/F ratio (i.e., an output of the A/F sensor) will have an extremely fuel lean value. The microcomputer 20 sets the air-fuel ratio measuring range thereof to the wide range R2. The sensor control circuit 30 controls the switch 44 and establishes the electrical connection between the operational amplifier 39 and the contact b to select a lower one (i.e., GB) of the amplification factors GB and GA. The engine ECU 25 analyzes the output of the A/F sensor to diagnose the operation of the A/F sensor.

Afterwards, when the A/F ratio is returned to the stoichiometry at time t2, the engine ECU 25 resumes the stoichiometric feedback control. The microcomputer 20 returns the air-fuel ratio measuring range thereof to the narrow range R1 and switches the connection of the operational amplifier 39 to the contact b to the contact a through the switch 44 to select the higher amplification factor GA.

When the vehicle has been started to be accelerated at time t3, so that the load on the engine is increased highly, the engine ECU 25 performs the rich feedback control. The microcomputer 20, like in the fuel-cut off mode, sets the air-fuel ratio measuring range thereof to the wide range R2. The sensor control circuit 30 controls the switch 44 to establish the electrical connection of the operational amplifier 39 to the contact b to select the lower amplification factor GB.

The advantages, as offered by the air-fuel ratio measuring apparatus of this embodiment, will be described below.

The sensor control circuit 30 is designed to select any one or two of the amplifying resistors 41 to 43 as the input resistor or the feedback resistor in the amplifier circuit 38 using the switch 44 to switch the amplification factor of the amplifier circuit 38 between the higher and lower ones. In other words, the sensor control circuit 30 is permitted to change the resolution in measuring the air-fuel ratio as required, thus ensuring desired accuracy in a selected air-fuel ratio measuring range.

The selection of the amplification factors of the amplifier circuit 38 is, as described above, achieved by turning on or off the switch 44 to select the resistance values of the input resistor and the feedback resistor in the amplifier circuit 38, thus eliminating the need for a plurality of operational amplifiers, as used in the conventional structure, as discussed in the introductory part of this application, to select one of a plurality of amplification factors. This permits the structure of the sensor control circuit 30 to be reduced in size and produced at a decreased cost, and the required number of terminals to be decreased.

The installation of the switch 44 on the signal input line leading to the minus input terminal of the operational amplifier 39 results in improved accuracy in amplifying the A/F output voltage in the amplifier circuit 38. Specifically, the signal input line to the operational amplifier 39 has typically a high impedance, so that the resistance component of the switch 44 may be ignored, thus resulting in improved accuracy in amplifying the signal in the amplifier circuit 38.

The microcomputer 20 is designed to switch between the narrow range R1 (near the stoichiometric air-fuel ratio) and the wide range R2 to sample the output of the A/F sensor as a function of the air-fuel ratio of a mixture charged into the engine, thereby enabling stoichiometric air-fuel ratio control (i.e., the stoichiometric feedback control) to be performed with high accuracy, the diagnosis of the A/F sensor to be made using an output of the A/F sensor during the fuel cut-off mode of the engine in the wide range R2, and the rich feedback control to be performed accurately when it is required to increase the load on the engine.

Figure 6:
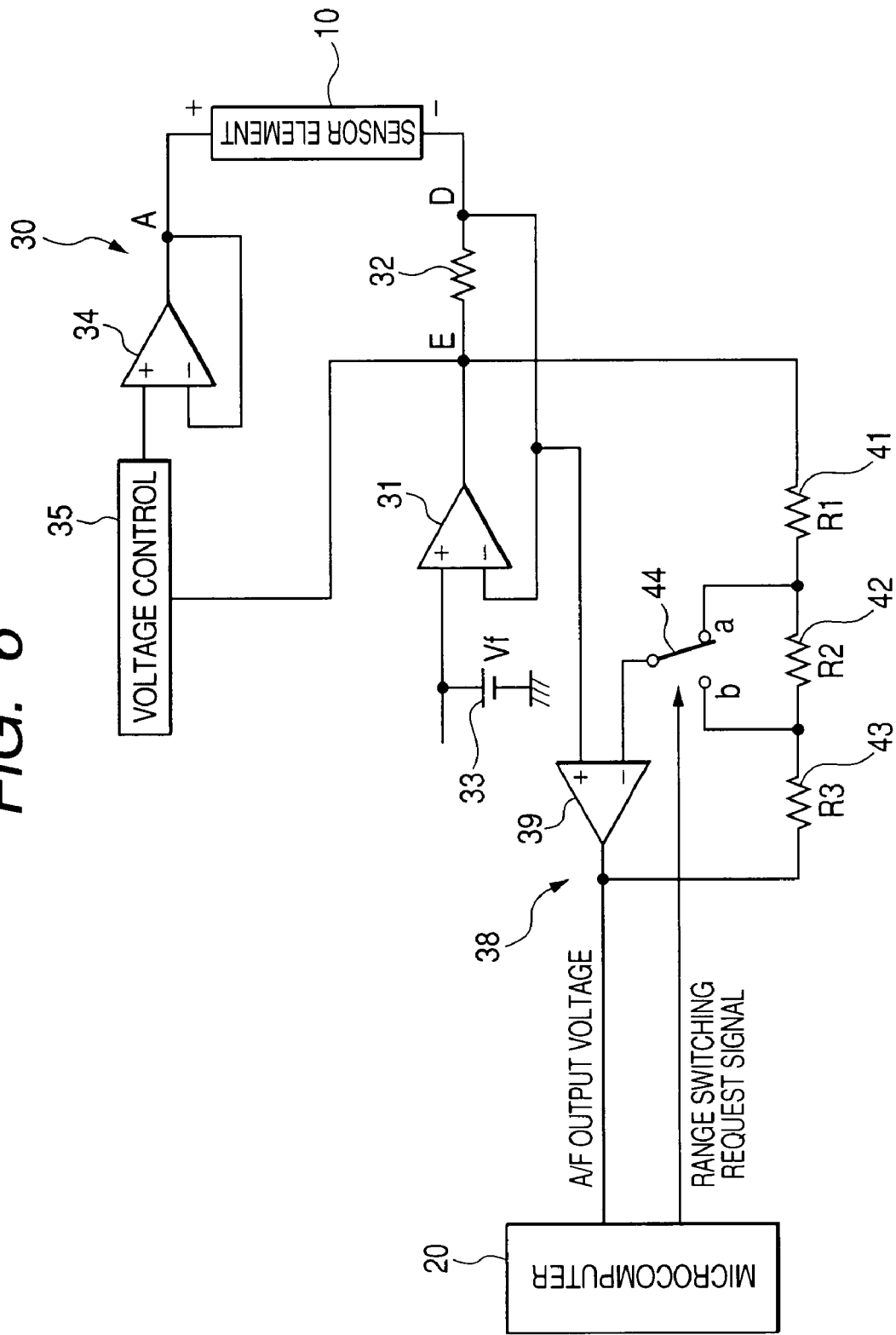
FIG. 6 is a circuit diagram which shows a structure of a sensor control circuit according to the second embodiment of the invention.

FIG. 6 illustrates the sensor control circuit 30 according to the second embodiment of the invention which is different from the first embodiment in that the current-measuring resistor 32 is connected to the negative terminal of the sensor element 10. The same reference numbers as employed in the first embodiment will refer to the same parts, and explanation thereof in detail will be omitted here.

The negative (−) terminal of the sensor element 10 connects with the reference voltage circuit 33 through the current-measuring resistor 32 and the operational amplifier 31. The positive (+) terminal of the sensor element 10 connects with the voltage application control circuit 35 through the operational amplifier 34. The voltage appearing at a junction D of the end of the current-measuring resistor 32 is kept at the same level as that of the reference voltage source 33 (i.e., the reference voltage Vf). The sensor element current Ip flows through the current-measuring resistor 32. The voltage appearing at the junction E changes with a change in the sensor element current Ip. When the exhaust gas of the engine is in the fuel lean state, that is, the exhaust gas results from burning of the lean mixture, the sensor element current Ip flows from the positive terminal to the negative terminal through the sensor element 10, so that the voltage at the junction E drops. Conversely, when the exhaust gas is the fuel rich state, the sensor element current Ip flows from the negative terminal to the positive terminal through the sensor element 10, so that the voltage at the junction E rises. The voltage application control circuit 35 works to monitor the voltage at the junction E and determine the target voltage Vp to be applied to the sensor element 10 as a function of the monitored voltage, for example, by look-up using the target applying voltage line LX1, as illustrated in FIG. 3. The voltage application control circuit 35 then controls the operational amplifier 34 to bring the voltage at the junction A into agreement with the target voltage Vp.

The amplifier circuit 38 connects with the junctions D and E leading to the ends of the current-measuring resistor 32. The A/F output voltage that is an output of the amplifier circuit 38 is inputted to the A/D converter of the microcomputer 20. The amplifier circuit 38 is made up of the operational amplifier 39, the series-connected amplifying resistors 41, 42, and 43, and the switch 44 made of, for example, a MOS transistor. Specifically, the amplifier circuit 38 has the same structure as the one in FIG. 1. The switch 44, like the first embodiment, works to establish the electrical connection of the operational amplifier 39 with the contact a or b selectively to change the amplification factor of the amplifier circuit 38 between the higher and lower one. When the switch 44 establishes, as illustrated in the drawing, the electrical connection between the operational amplifier 39 and the contact a, the amplifier circuit 38 has the amplification factor GA, as represented by equation (1), as described above. Alternatively, when the switch 44 establishes the electrical connection between the operational amplifier 39 and the contact b, the amplifier circuit 38 has the amplification factor GB, as represented by equation (2), as described above.

The structure of the sensor control circuit 30 of this embodiment offers the same effects, as described in the first embodiment.

Figure 7A:
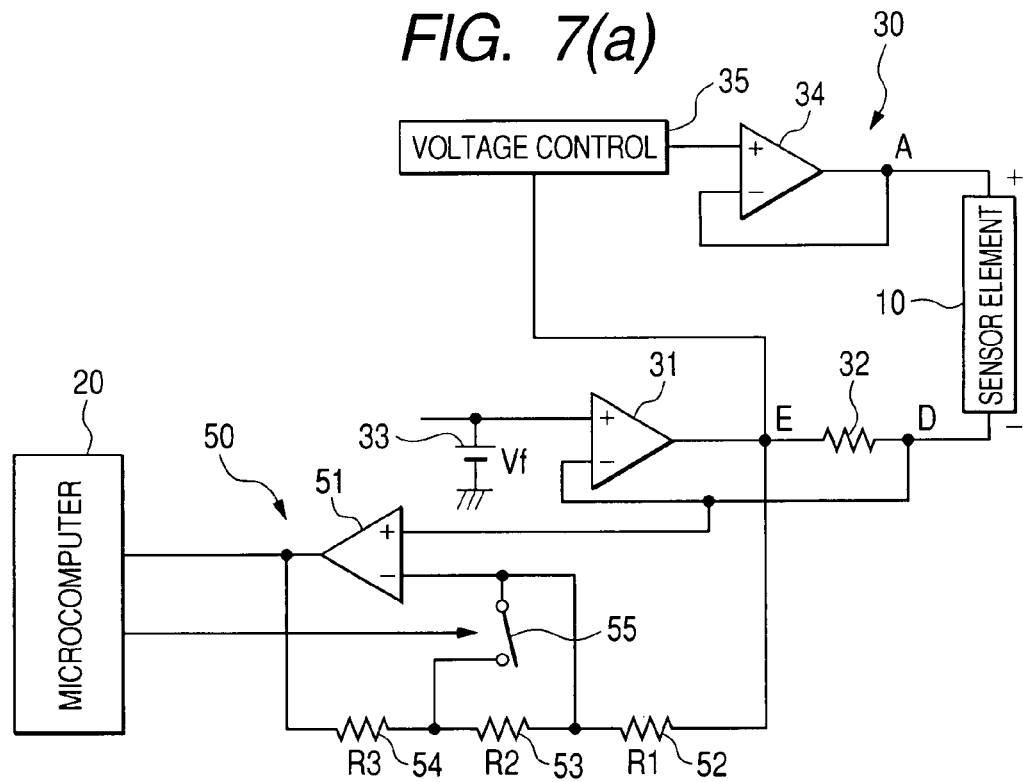
FIG. 7($a$) is a circuit diagram which shows a structure of a sensor control circuit according to the third embodiment of the invention.

FIG. 7(a) illustrates the sensor control circuit 30 according to the third embodiment of the invention which is a modification of the one of the second embodiment in FIG. 6. The same reference numbers as employed in FIG. 6 will refer to the same parts, and explanation thereof in detail will be omitted here.

The sensor control circuit 30 includes an amplifier circuit 50 connecting with the junctions D and E leading to the ends of the current-measuring resistor 32. The amplifier circuit 50 works to output the A/F output voltage to the A/D converter of the microcomputer 20. The amplifier circuit 50 is made up of an operational amplifier 51, series-connected amplifying resistors 51, 52, and 53, and a switch 55 made of, for example, a MOS transistor. The resistors 51, 52, and 53 have resistance values R1, R2, and R3, respectively.

The amplifier circuit 50 has a signal input line which extends from the minus terminal of the operational amplifier 51. The signal input line has two branch lines one of which connects with a junction between the resistors 52 and 53 and the other connects with a junction between the resistors 53 and 54. The switch 55 is disposed the minus terminal of the operational amplifier 51 and the junction of the resistors 53 and 54. The switch 55 is of a normally open type which is closed in response to the range switching request signal outputted from the microcomputer 20.

When the switch 55 is in the off-state or opened, the amplifying resistor 52 serves as the input resistor in the amplifier circuit 50, and the amplifying resistors 53 and 54 serve as the feedback resistor in the amplifier circuit 50. The amplification factor GC of the amplifier circuit 50 in such a condition will, thus, be given by an equation below.

$$GC=(R2+R3)/R1 \quad (3)$$

Alternatively, when the switch 55 is on the on-state or closed, the amplifying resistor 52 serves as the input resistor in the amplifier circuit 50, and the amplifying resistor 54 serves as the feedback resistor in the amplifier circuit 50. The amplification factor GD of the amplifier circuit 50 in such a condition will, thus, be given by an equation below.

$$GD=R3/R1 \quad (4)$$

Comparison between the equations (3) and (4) shows that the amplification factor GC is greater than the amplification factor GD. Specifically, when the switch 55 is switched from the off- to on-state, it will cause the amplification factor of the amplifier circuit 50 to be changed from the higher to the lower one.

FIG. 7(*b*) illustrates a modification of the sensor control circuit 30 of FIG. 7(*a*).

The amplifier circuit 50 has two amplifying resistors 56 and 57 serving as the input resistor and an amplifying resistor 58 serving as the feedback resistor. A switch 59 which is made of, for example, a MOS transistor is connected in series with the amplifying resistor 56. The switch 59 is of a normally closed type which is opened in response to the range switching request signal outputted from the microcomputer 20. The amplifying resistors 56, 57, and 58 have resistance values R1, R2, and R3, respectively.

When the switch 59 is in the off-state or closed, a combination of the amplifying resistors 56 and 57 serves as the input resistor in the amplifier circuit 50, and the amplifying resistor 58 serves as the feedback resistor in the amplifier circuit 50. The amplification factor GE of the amplifier circuit 50 in such a condition will, thus, be given by an equation below.

$$GE=R3/Rx \quad (5)$$

where Rx is a combined resistance of the amplifying resistors 56 and 57.

Alternatively, when the switch 55 is on the on-state or opened, the amplifying resistor 57 serves as the input resistor in the amplifier circuit 50, and the amplifying resistor 58 serves as the feedback resistor in the amplifier circuit 50. The amplification factor GF of the amplifier circuit 50 in such a condition will, thus, be given by an equation below.

$$GF=R3/R2 \quad (6)$$

Comparison between the equations (5) and (6) shows that the amplification factor GE is greater than the amplification factor GF. Specifically, when the switch 59 is switched from the off- to on-state, it will cause the amplification factor of the amplifier circuit 50 to be changed from the higher to the lower one.

The structure of either of FIGS. 7(*a*) and 7(*b*) has an always-on connection line which connects the operational amplifier 51 and any of the amplifying resistors 56 to 58 constantly without the switch 55 or 59, thus avoiding temporal opening of the signal input line to the amplifier circuit 50 upon switching of the switch 55 or 59. This ensures the stability of the A/F output voltage to be produced by the amplifier circuit 50.

Figure 8A:
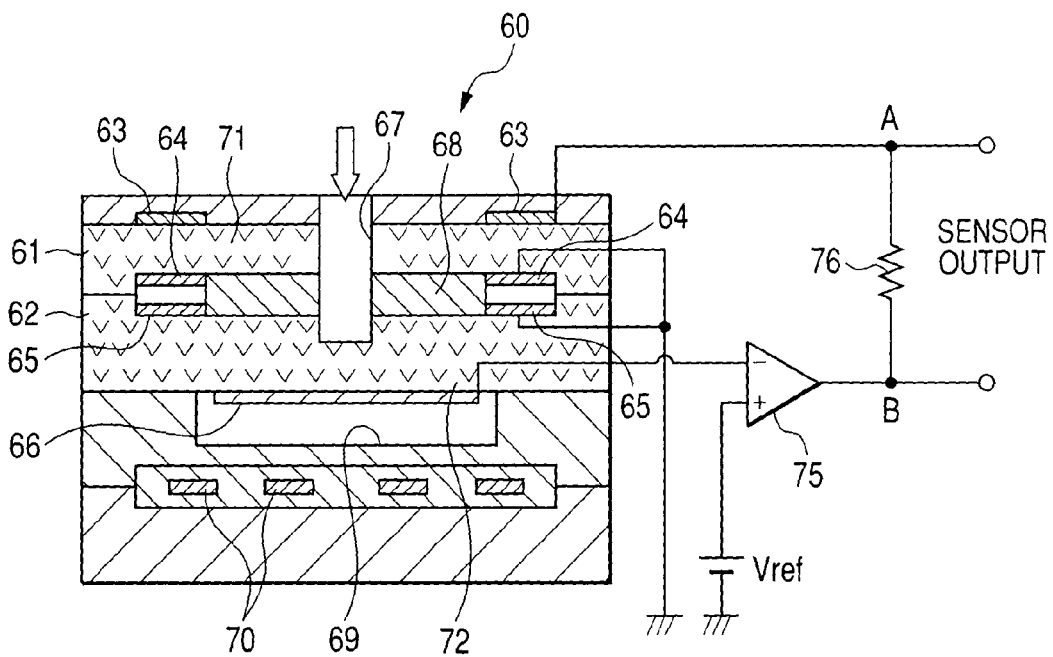
FIG. 8($a$) is a transverse sectional view which shows a sensor element of a gas concentration measuring apparatus according to the fourth embodiment of the invention.
Figure 8B:
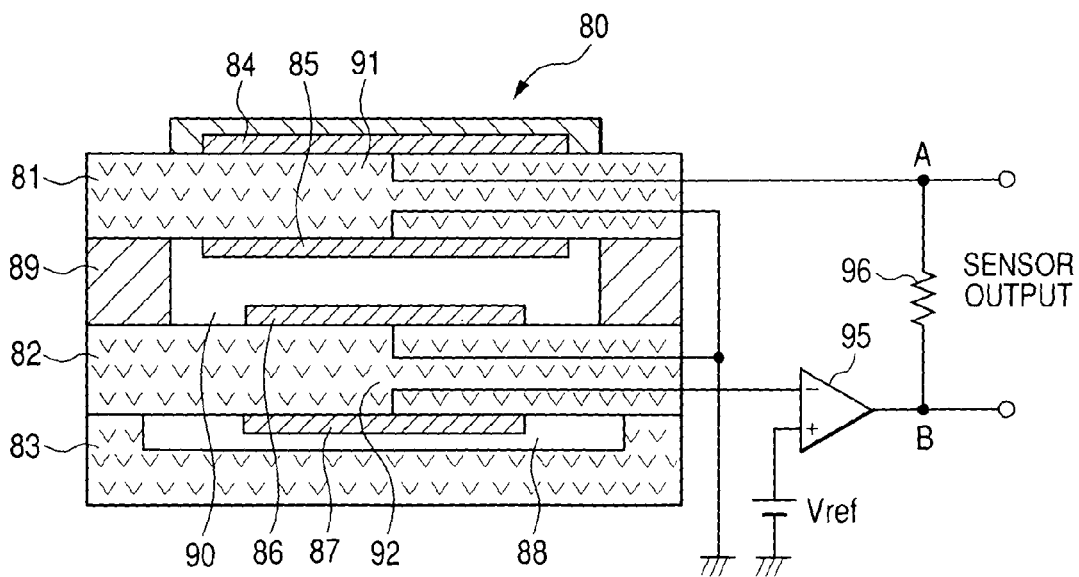

FIG. 8(*a*) illustrates a sensor element 60 according to the fourth embodiment of the invention which is different in structure from the one illustrated in FIG. 2 and may be fabricated in the A/F sensor as used in the first embodiment instead of the sensor element 10.

The sensor element 60 includes a laminate of two solid electrolyte layers 61 and 62. The solid electrolyte layer 61 has electrodes 63 and 64 affixed to opposed surfaces thereof. Similarly, the solid electrolyte layer 62 has electrodes 65 and 66 affixed to opposed surfaces thereof. Each of the electrodes 63, 64, and 65 is viewed in the drawing as being made up of right and left separate parts, but, it is, in practice, formed by a single plate having a connecting portion (not shown) extending in a transverse direction in the drawing.

The solid electrolyte layer 61 and the electrodes 63 and 64 constitute a pump cell 71. The solid electrolyte layer 62 and the electrodes 65 and 66 constitute an oxygen sensor cell 72. The sensor element 60 also includes a gas inlet 67 through which exhaust gas of the automotive engine enters and a porous diffusion layer 68, an air duct 69, and a heater 70. The structure and operation of this type of sensor element are disclosed in, for example, U.S. Pat. No. 6,295,862 B1, assigned to the same assignee as that of this application, disclosure of which is incorporated herein by reference.

The potential at the electrode 66 of the oxygen sensor cell 72 is inputted to a minus input terminal of a comparator 75. The reference voltage Vref is inputted to a plus input terminal of the comparator 75. A current-measuring resistor 76 is connected between the electrode 63 of the pump cell 71 and an output of the comparator 75. The output of the sensor element 60 is developed at junctions A and B leading to ends of the current-measuring resistor 76.

In operation, the oxygen sensor cell 72 works to produce an electromotive force which has one of two discrete values (e.g., 0V and 0.9V) selectively as a function of whether the exhaust gas is on the rich side or the lean side of a stoichiometric point corresponding to a stoichiometric air-fuel ratio of mixture charged into the engine. For instance, when the exhaust gas is on the lean side, the oxygen sensor cell 72 produces a lower electromotive force, so that the level of output of the comparator 75 (i.e., the voltage at the junction B) rises. This causes the current to flow from the junction B to the junction A through the current-measuring resistor 76. Conversely, when the exhaust gas is on the rich side, the oxygen sensor cell 72 produces a higher electromotive force, so that the level of output of the comparator 75 (i.e., the voltage at the junction B) drops. This causes the current to flow from the junction A to the junction B through the current-measuring resistor 76. The oxygen sensor cell 72 is generally also called an electromotive force cell or an oxygen concentration sensor cell.

FIG. 8(*b*) shows a sensor element 80 according to the fifth embodiment of the invention which may be built in the A/F sensor, as employed in each of the above embodiments.

The sensor element 100 includes three solid electrolyte layers 81, 82, and 83. The solid electrolyte layer 81 has electrodes 84 and 85 affixed to opposed surfaces thereof. Similarly, the solid electrolyte layer 82 has electrodes 86 and 87 affixed to opposed surfaces thereof. The solid electrolyte layer 81 and the electrodes 84 and 85 form a pump cell 91. The solid electrolyte layer 82 and the electrodes 86 and 87 form an oxygen sensor cell 91. The solid electrolyte layer 83 forms a wall defining an oxygen reference chamber 88. The sensor element 80 is, like the sensor element 10, of a laminated structure. The sensor element 80 also includes a porous diffusion layer 89 and a gas chamber 90 into which exhaust gas of the automotive engine enter. The oxygen sensor cell 92 operates, like the oxygen sensor cell 72 illustrated in FIG. 8(a), as an electromotive force cell or an oxygen concentration sensor cell.

The potential at the electrode 87 of the oxygen sensor cell 92 is inputted to a minus input terminal of a comparator 95. The reference voltage Vref is inputted to a plus input terminal of the comparator 95. A current-measuring resistor 96 is connected between the electrode 84 of the pump cell 91 and an output of the comparator 95. The output of the sensor element 80 is developed at junctions A and B leading to ends of the current-measuring resistor 96. In operation, when the exhaust gas is on the lean side, it will cause the current to flow from the junction B to the junction A through the current-measuring resistor 96. Conversely, when the exhaust gas is on the rich side, it will cause the current to flow from the junction A to the junction B through the current-measuring resistor 96.

Figure 9:
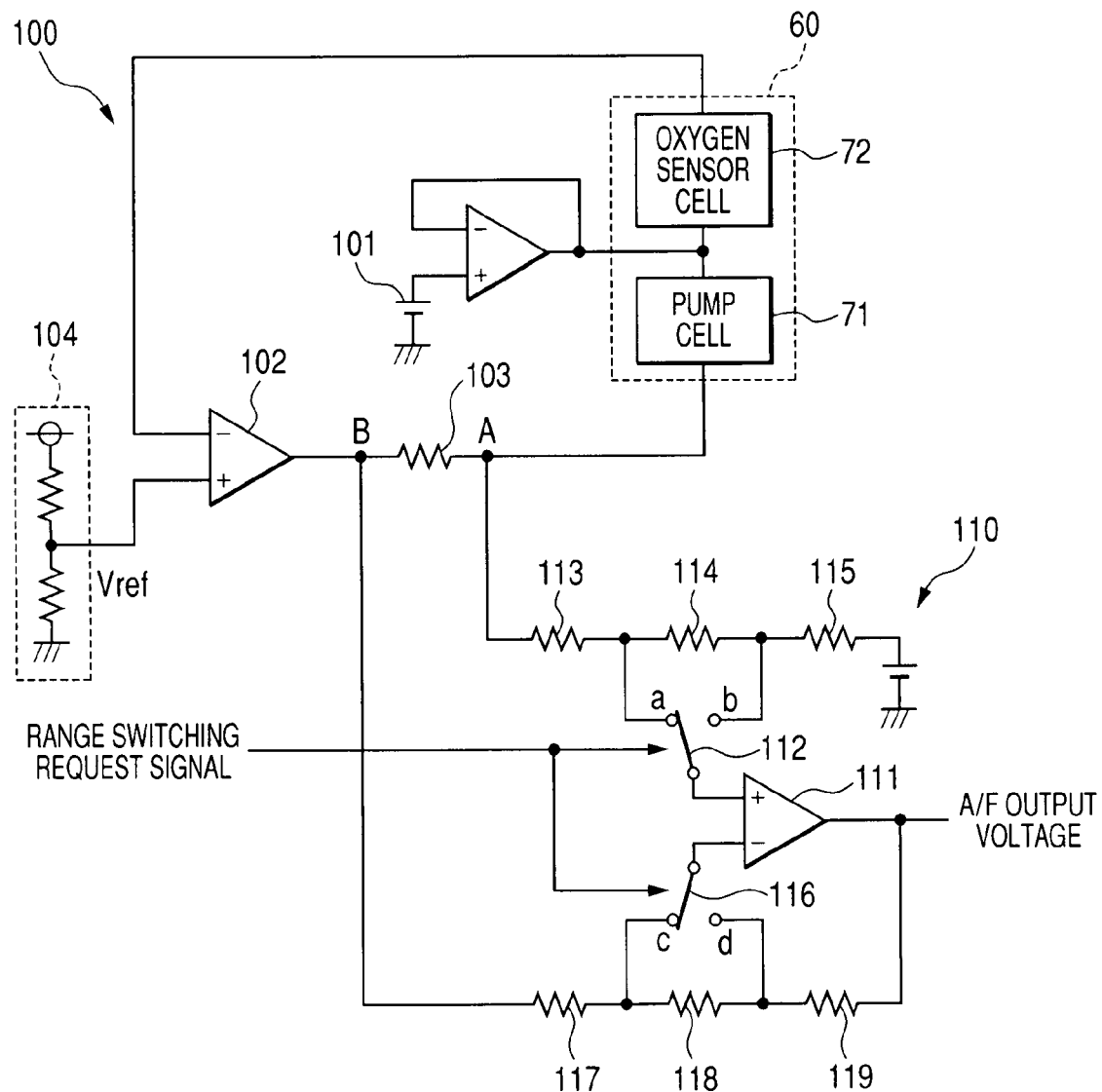
FIG. 9 is a circuit diagram which shows a sensor control circuit for the sensor element of FIG. 8($a$)

FIG. 9 shows a sensor control circuit 100 for the two-cell sensor cell 60, as illustrated in FIG. 8(a).

The sensor control circuit 100 includes a reference voltage source 101, an operation amplifier 102, a current-measuring resistor 103, a reference voltage generator 104, and a differential amplifier 110. The reference voltage source 101 is connected to a joint of the pump cell 71 and the oxygen sensor cell 72. The pump cell 71, the oxygen sensor cell 72, the operational amplifier 102, and the current-measuring resistor 103 forms a closed loop. The reference voltage generator 104 is connected to a non-inverting input terminal (+ terminal) of the operational amplifier 102 to output a reference voltage Vref of 0.45V to the operational amplifier 102. When the exhaust gas is on the lean side, it will cause the current to flow from the junction B to the junction A through the current-measuring resistor 103. Conversely, when the exhaust gas is on the rich side, it will cause the current to flow from the junction A to the junction B through the current-measuring resistor 103. Note that the operational amplifier 102 corresponds to the operational amplifier 75, as illustrated in FIG. 8(a), and the current-measuring resistor 103 corresponds to the current-measuring resistor 76, as illustrated in FIG. 8(a). The sensor control circuit 100 works to control the operation of the pump cell 71 so as to bring the output voltage of the oxygen sensor cell 72 into agreement with a selected value in a feedback control mode. The structure and operation of a feedback control circuit are well known in the art, and explanation thereof in detail will be omitted here.

The differential amplifier 110 is connected to the junctions A and B leading to ends of the current-measuring resistor 103. The A/F output voltage that is an output of the differential amplifier 110 is outputted to a microcomputer (not shown) such as the one illustrated in FIG. 1. The differential amplifier 110 includes an operational amplifier 111, amplifying resistors 113, 114, 115, 117, 118, and 119, and switches 112 and 116. The switch 112 is disposed on a signal input line leading to a positive input terminal (i.e., a non-inverting input terminal) of the operational amplifier 111. The switch 112 has contacts a and b which connect with ends of the amplifying resistor 114 that is a middle one of the amplifying resistors 113 to 115 connected in series. The switch 112 normally establishes an electrical connection between the contact a and the positive input terminal of the operational amplifier 111.

The switch 116 is disposed on a signal input line leading to a negative input terminal (i.e., an inverting input terminal) of the operational amplifier 111. The switch 116 has contacts c and d which connect with ends of the amplifying resistor 118 that is a middle one of the amplifying resistors 117 to 119 connected in series. The switch 116 normally establishes an electrical connection between the contact c and the negative input terminal of the operational amplifier 111.

When the range switching request signal is outputted from the microcomputer, the switch 112 establishes an electrical connection between the operational amplifier 111 and the contact b. Similarly, the switch 116 establishes an electrical connection between the operational amplifier 111 and the contact d. This results in switching between a higher and a lower amplification factor in the differential amplifier 110. The switching between the amplification factors, that is, between the narrow and wide ranges R1 and R2 is made in the same manner as described in the first embodiment, and explanation thereof in detail will be omitted here.

Figure 10:
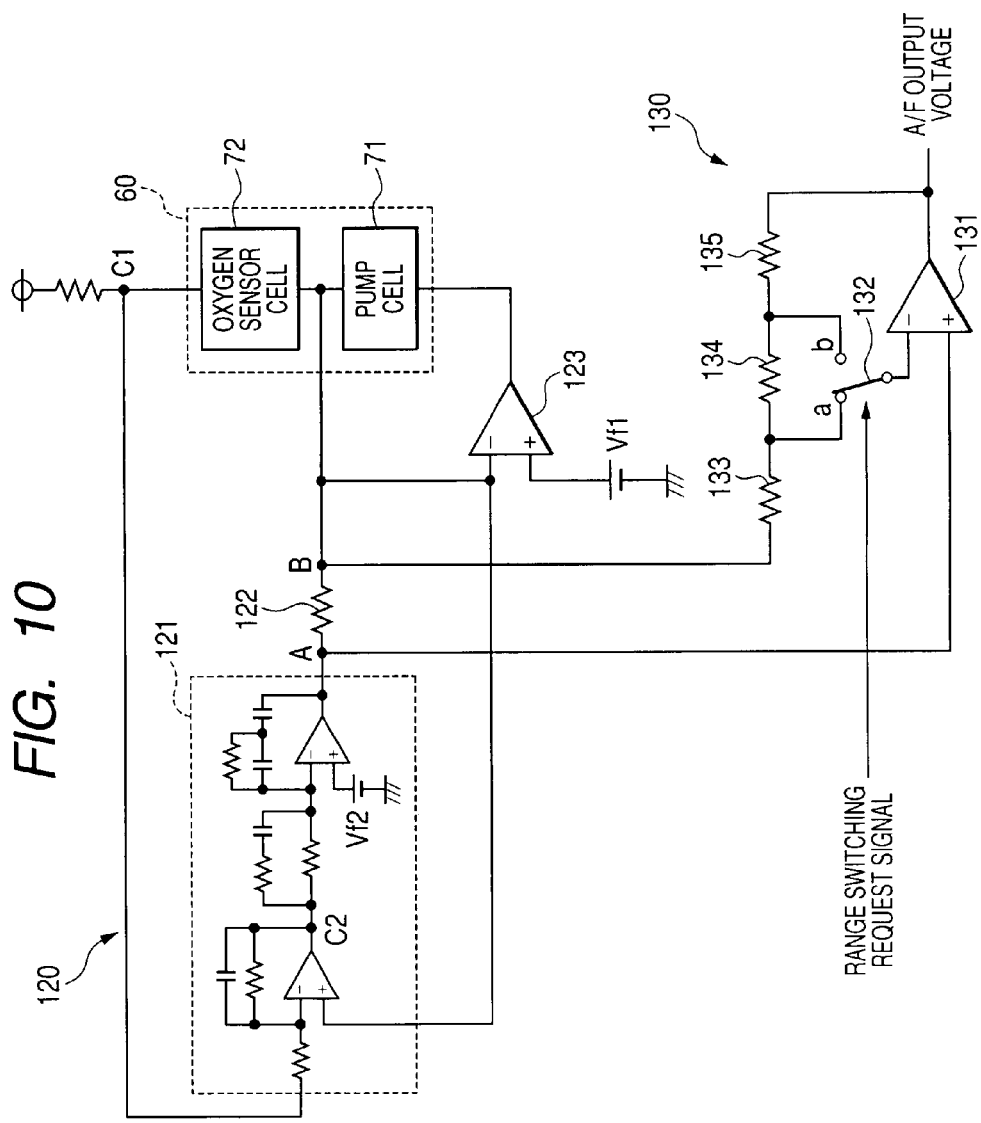
FIG. 10 is a circuit diagram which shows a modification of the sensor control circuit of FIG. 9.

FIG. 10 illustrates a sensor control circuit 120 which is a modification of the one of FIG. 9.

The sensor control circuit 120 includes a feedback circuit 121, a current-measuring resistor 122, an operational amplifier 123, and an amplifier circuit 130.

The voltage which is identical with a reference voltage Vf1 (e.g., 3V) is applied to a joint between the pump cell 71 and the oxygen sensor cell 71 through the operational amplifier 123, so that the voltage appearing at the junction B is kept at, for example, 3V. The oxygen sensor cell 72, the feedback circuit 121, and the current-measuring resistor 122 forms a closed loop. The feedback circuit 121 has installed therein a reference voltage source providing a reference voltage Vf2 of, for example, 2.55V.

For example, when the exhaust gas is on the rich side, the electromotive force, as developed by the oxygen sensor cell 71, elevates the voltage at a junction C1 up to 3.45V, thereby causing the voltage at a junction C2 in the feedback circuit 121 to drop, which leads to an elevation in voltage at the junction A. Specifically, when the exhaust gas is on the rich side, it will cause the current to flow from the junction A to the junction B through the current-measuring resistor 122. Conversely, when the exhaust gas is on the lean side, it will cause the current to flow from the junction B to the junction A through the current-measuring resistor 122.

The amplifier circuit 130 is connected to the junctions A and B leading to ends of the current-measuring resistor 122. The A/F output voltage that is an output of the amplifier circuit 130 is outputted to a microcomputer (not shown) such as the one illustrated in FIG. 1. The amplifier circuit 130 includes an operational amplifier 131, amplifying resistors 133, 134, and 135, and a switch 132. The switch 132 is disposed on a signal input line leading to a negative input terminal (i.e., an inverting input terminal) of the operational amplifier 131. The switch 132 has contacts a and b which connect with ends of the amplifying resistor 134 that is a middle one of the amplifying resistors 133 to 135 connected in series. The switch 132 normally establishes an electrical connection between the contact a and the negative input terminal of the operational amplifier 131.

When the range switching request signal is outputted from the microcomputer, the switch 132 establishes an electrical connection between the operational amplifier 131 and the contact b, thereby resulting in switching between a higher and a lower amplification factor in the amplifier circuit 130. The switching between the amplification factors, that is, between the narrow and wide ranges R1 and R2 is made in the same manner as described in the first embodiment, and explanation thereof in detail will be omitted here.

Figure 7B:
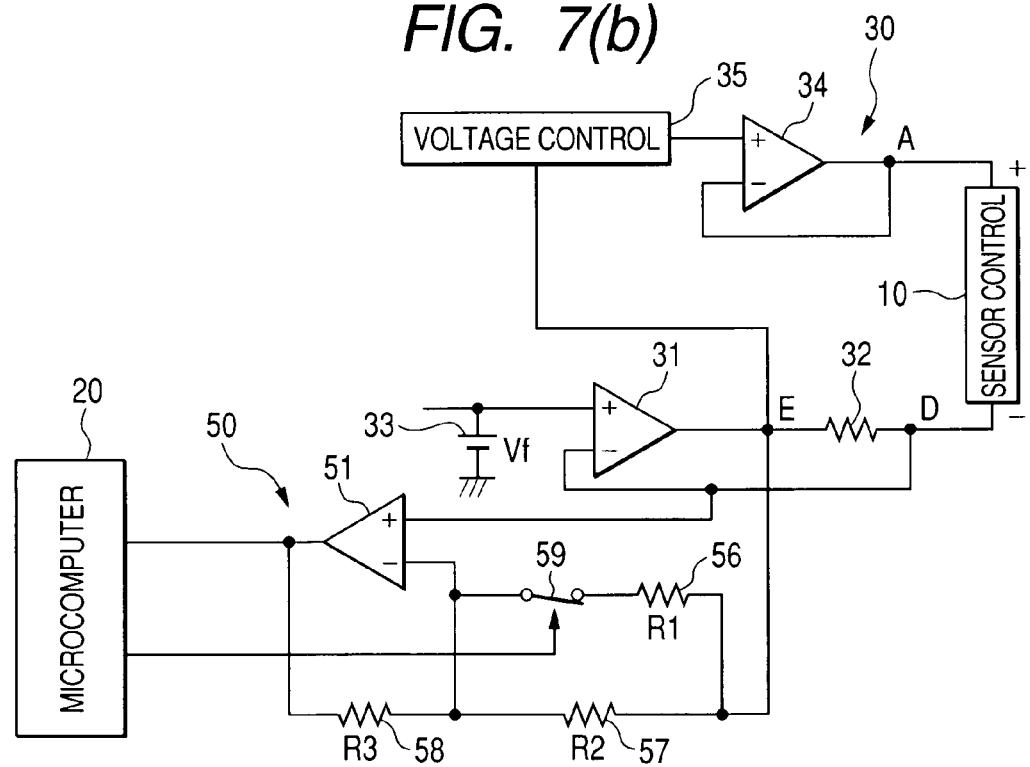

Each of the sensor control circuits 110 and 120, as illustrated in FIGS. 9 and 10, may be equipped with either of the amplifier circuits 130, as illustrated in FIGS. 7(a) and 7(b).

Each of the sensor control circuits of the above embodiments works to have the higher amplification factor for the narrow range R1 when the switch in the amplifier circuit is in the off-state, but however, may be designed to have the lower amplification factor for the wide range R2 when the switch in the amplifier circuit is in the off-state.

In each of the above embodiments, the narrow range R1 is defined between A/F ratio=13:1 and A/F ratio=18.1, while the wide range R2 is defined between A/F ratio=10:1 and the atmospheric air-equivalent value, but however, the wide range R2 may alternatively include at least one of the atmospheric air-equivalent value when the engine is undergoing the fuel cut and the value of the A/F ratio during rich air-fuel ratio burning of the engine. Each of the sensor control circuits of the above embodiments may alternatively be designed to select one of three or more air-fuel ratio measuring range as required.

Each of the sensor control circuits of the above embodiments may also be designed to select one of three or more amplification factors, as required, which is achieved in the same manner as described above by controlling the operations of the switches to distribute the amplifying resistors into the input resistor and the feedback resistor in the amplifier circuit.

The gas concentration measuring apparatus, as described in each of the above embodiments, may be used with a composite gas concentration measuring sensor which includes first and second cells made of a solid electrolyte body. The first cell works as a pump cell to pump oxygen molecules out of or into a first gas chamber formed in a sensor body and output a signal indicative of the concentration of the pumped oxygen molecules. The second cell works as a sensor cell to produce a signal indicative of the concentration of a preselected component of gasses flowing into a second gas chamber from the first gas chamber. For example, the composite gas concentration measuring sensor may be used to measure the concentration NOx contained in exhaust gasses of the automotive engine. Further, the composite gas concentration measuring sensor may be designed to have a third cell serving as a monitor cell or a second pump cell to produce an electromotive force as a function of concentration of oxygen molecules remaining in the second gas chamber.

The gas concentration measuring apparatus in each of the embodiments may also be designed to measure the concentration of HC or CO contained in the exhaust gases of the automotive engine. The measurement of concentration of HC or CO is achieved by pumping excessive oxygen ($O_2$) out of the first gas chamber using the pump cell and decomposing HC or CO contained in the gasses entering the second gas chamber using the sensor cell to produce an electric signal indicative of the concentration of HC or CO.

The gas concentration measuring apparatus in each of the embodiments may also be designed to measure the concentration of gasses other than the exhaust gases of automotive engines.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas concentration measuring apparatus comprising:
a gas sensor equipped with a sensor element which is made of a solid electrolyte and works to produce a sensor current upon application of voltage thereto as a function of a concentration of a selected gas;
a current-measuring resistor used to measure the sensor current flowing through said sensor element;
an amplifier circuit equipped with an operational amplifier and a plurality of amplifying resistors, said amplifier circuit working to amplify the sensor current, as measured through said current-measuring resistor;
a gas concentration measuring circuit working to determine the concentration of the gas based on the sensor current, as amplified by said amplifier circuit; and
a switch operating to switch an electrical connection relation between the operational amplifier and the plurality of amplifying resistors to selectively distribute the plurality of amplifying resistors into an input resistor and a feedback resistor for the operational amplifier to thereby change an amplification factor of said amplifier circuit;
wherein said switch is disposed on an input line extending from said current-measuring resistor and the operational amplifier;
wherein the plurality of amplifying resistors are three resistors connected in series, and wherein said switch operates to allow one of the three resistors to operate as an input resistor, a second resistor to operate as a feedback resistor, and the third resistor to operate as either a second input or second feedback resistor.

2. A gas concentration measuring apparatus as set forth in claim 1, wherein said gas concentration measuring circuit is designed to determine the concentration of the gas in a selected one of a wider measuring range and a narrower measuring range, when it is required to select the narrower measuring range, said gas concentration measuring circuit controlling operation of said switch so as to increase the amplification factor of said amplifier circuit, when it is required to select the wider measuring range, said gas concentration measuring circuit controlling the operation of said switch so as to decrease the amplification factor of said amplifier circuit.

3. A gas concentration measuring apparatus as set forth in claim 1, further comprising an input line extending from said current-measuring resistor and the operational amplifier, said input line including a first and a second branch line which extend parallel to each other, the first branch line having at least one of the amplifying resistors and said switch disposed thereon, the second branch line having the other amplifying resistors disposed thereon.

4. A gas concentration measuring apparatus as set forth in claim 1, wherein the selected gas is a selected gas component in exhaust emissions from an internal combustion engine, said gas concentration measuring apparatus calculating a concentration of the selected gas component for determining an air-fuel ratio of a mixture charged into the internal combustion engine in a selected one of a narrow range defined around a stoichiometric air-fuel ratio and a wide range which is wider than the narrow range and extends from a fuel rich air-fuel ratio to a fuel lean air-fuel ratio, and wherein said gas concentration measuring circuit controls the operation of said switch so as to have amplification factors in said amplifier circuit which are different between the narrow and wide ranges.

5. A gas concentration measuring apparatus as set forth in claim 4, wherein the wide range is defined to include at least one of an atmospheric air-equivalent value when the internal combustion engine is undergoing a fuel cut and a value of an air-fuel ratio during rich air-fuel ratio burning of the internal combustion engine.

6. A gas concentration measuring apparatus as set forth in claim 1, wherein said switch operates to switch the electrical connection relation between the operational amplifier and the plurality of amplifying resistors to change the amplification factor to a desired one.

* * * * *